United States Patent [19]

Umemoto et al.

[11] Patent Number: 5,104,491
[45] Date of Patent: Apr. 14, 1992

[54] METHOD FOR PURIFYING PENTACHLORONITROBENZENE BY SOLID BASE TREATMENT

[75] Inventors: Mitsumasa Umemoto; Ryuichi Mita; Yoshitsugu Kono; Hiroshi Maeda, all of Omuta, Japan

[73] Assignee: Mitsui Toatsu Chemicals, Inc., Tokyo, Japan

[21] Appl. No.: 668,211

[22] Filed: Mar. 12, 1991

[30] Foreign Application Priority Data

Mar. 16, 1990 [JP] Japan ................................ 2-63961

[51] Int. Cl.$^5$ .................. B01D 3/10; C07C 205/12
[52] U.S. Cl. ................................ 203/7; 203/33; 203/36; 203/37; 203/91; 203/DIG. 22; 568/938
[58] Field of Search ............. 203/33, 36, 37, 29, 203/73, 7, DIG. 11, 91, 99, DIG. 22, 41, 47; 568/938, 937

[56] References Cited

U.S. PATENT DOCUMENTS

| | | | |
|---|---|---|---|
| 3,660,248 | 5/1972 | Tsao | 203/37 |
| 3,846,253 | 11/1974 | Obrecht | 203/37 |
| 4,147,732 | 4/1979 | Mendiratta | 568/938 |
| 4,461,918 | 7/1984 | Gay et al. | 568/938 |
| 4,842,696 | 6/1989 | Cazares | 568/938 |

FOREIGN PATENT DOCUMENTS

| | | | |
|---|---|---|---|
| 62-230752 | 10/1987 | Japan | 568/938 |
| 63-17849 | 1/1988 | Japan | 568/938 |

*Primary Examiner*—Wilbur Bascomb, Jr.
*Attorney, Agent, or Firm*—Burns, Doane, Swecker & Mathis

[57] ABSTRACT

Crude pentachloronitrobenzene containing hexachlorobenzene and small amounts of acids is treated in the molten state or in a mixture solution of nitrobenzene or chloronitrobenzenes with an inorganic basic substance and then subjected to a distillation under reduced pressure.

15 Claims, No Drawings

METHOD FOR PURIFYING PENTACHLORONITROBENZENE BY SOLID BASE TREATMENT

BACKGROUND OF THE INVENTION

1. Field of the Invention

This invention relates to a method for purifying pentachloronitrobenzene (hereinafter referred to as PCNB), and more particularly, to an improved method for purifying PCNB under reduced pressure so as to decrease the amount of an impurity, hexachlorobenzene (hereinafter referred to as HCB), contained in PCNB produced industrially. PCNB can be used as a germicidal agent for soil in agriculture.

2. Description of the Related Art

It has been recently a worldwide problem that agricultural chemicals and impurities and other compounds present therein cause environmental pollution. PCNB is already widely used as a germicidal agent for soil and is also included in agricultural agents. It is highly desirable to reduce the contents of undesirable compounds contained therein such as HCB and the like to make the quality of PCNB much purer.

For example, in U.S.A., a Revised PCNB Registration Standard was issued in April 1982 by the U.S. Environmental Protection Agency to the effect that a new technique should be practiced to reduce the content of HCB in PCNB to 0.5 weight % or lower after March 1983 and to 0.1 weight % or lower after April 1988.

Heretofore, there are known various industrial methods for Producing PCNB. Main methods are processes for producing PCNB by chlorinating nitrobenzene or chloronitrobenzenes as disclosed in Khim. Prom., 1968, 44 (5), 334 etc. and processes for producing PCNB by nitration of pentachlorobenzene disclosed in U.S. Pat. Nos. 4,026,955, 4,057,590, 4,147,732 etc.

However, in the former method it is inevitable to produce HCB as a by-product by the perchlorination reaction and in the latter method HCB is formed as a by-product upon nitration and furthermore there is a significant problem that the starting material, pentachlorobenzene, is not always commercially available.

Recently Japanese Patent Application Laid-open No. 60-174748 disclosed a process for producing a highly pure PCNB comprising reacting HCB with sodium hydrogensulfide to form sodium pentachlorothiophenolate followed by reaction with a mixed acid to produce a highly pure PCNB containing a small amount of HCB.

However, there are problems in this process in that highly poisonous specific chemical substances are used as starting materials and HCB possibly remains depending upon the reaction conditions.

As is clear from the above discussion it is difficult at the present technical level to suppress the side reaction forming HCB in the reaction and to produce a highly pure PCNB containing only a very small amount of HCB.

On the other hand, there are mainly two methods for purifying PCNB containing HCB as an impurity to obtain a highly pure PCNB having a reduced HCB content.

One is a method comprising recrystallizing crude PCNB from a benzene-methanol system followed by subjecting the PCNB to column chromatography using an activated carbon column. A method for preparing a PCNB standard sample is disclosed in "Nogyo Kotei Kensaho Shokai" (Details of Agricultural Official Test Method), published by Nanko-do.

The other is a method comprising subjecting crude PCNB to silica gel column chromatography using carbon tetrachloride alone or a mixed solvent of carbon tetrachloride and a saturated hydrocarbon liquid (Japanese Patent Application Laid-open No. 53-95926).

Both purification methods are suitable for obtaining a highly pure PCNB in a laboratory, but are of less industrial value because large amounts of solvents and carriers are necessary.

In view of the present state of the art for producing a highly pure PCNB containing a small amount of HCB, the present inventors have found as a result of an intensive research on industrial purification methods that PCNB decomposes at temperatures higher than 250° C. resulting in an increase in HCB while at 250° C. or lower the decomposition hardly occurs and HCB and PCNB can be fractionated though the possibility is very narrow, and have proposed a method for purifying PCNB by distillation under reduced pressure at 150°-250° C. (Japanese Patent Laid-Open No. 62-230752).

According to the above-mentioned method, impurities such as tri- and tetrachloronitrobenzenes and the like as reaction intermediates as well as HCB contained in crude PCNB, have boiling points lower than PCNB and therefore, can be removed as initial distillate fractions by distillation under reduced pressure to enhance the purity of PCNB. After removing the impurities, the PCNB remaining in the bottom of column can be taken out as a pure PCNB or the PCNB is further subjected to distillation to obtain a highly pure PCNB. However, in this prior art purification method by distillation under reduced pressure, allowable impurities other than HCB are not mentioned in detail.

As mentioned above, there are known methods of producing PCNB such as chlorination of nitrobenzene or nitrochlorobenzenes and nitration of pentachlorobenzene. In the former method, chlorosulfonic acid is used as a reaction solvent while, in the latter method, a mixed acid is used as a nitration agent.

In each method, most of PCNB thus produced in the reaction is precipitated together with a by-product, HCB, outside of the reaction system, and therefore, after the reaction, the reaction mixture is poured into a large amount of water or the reaction mixture is directly subjected to a solid-liquid separation procedure, and then washed with water and, if necessary, washed with an alkaline aqueous solution followed by further dehydration or drying to isolate crude PCNB.

The crude PCNB thus isolated is treated in a purification step, but it is difficult to remove completely acids such as sulfuric acid, hydrogen chloride and the like included in the crystals. Therefore, inorganic acids such as sulfuric acid, hydrogen chloride and the like are present though the amounts are small, and sometimes sodium sulfate as well as organic impurities such as HCB and the like exist in the crude PCNB.

In fact, according to the investigation by the present inventors, it has been found that crude PCNB produced by the chlorination of nitrobenzene or chloronitrobenzenes contains about 1,000–5,000 ppm of sulfate ion and about 100–500 ppm of chloride ion and the pH is considerably acidic, that is, 4 or less.

In addition, it has been found that the presence of a small amount of acid accelerates the decomposition of PCNB depending on the temperature conditions upon purification by distillation under reduced pressure resulting in formation of HCB, and in particular, when pure PCNB is obtained as a bottom residue after distillation under reduced pressure, the quality of pure PCNB is deteriorated.

Furthermore, the presence of such acids in crude PCNB causes corrosion of metal materials such as stainless steel in the distillation step and therefore, materials to be used for apparatuses and machinery of the distillation equipment are limited accordingly.

SUMMARY OF THE INVENTION

It is an object of the present invention to provide a method for producing pure PCNB easily and industrially.

It is another object of the present invention to provide a method for purifying crude PCNB by efficiently removing acids contained therein before purification by distillation under reduced pressure.

It is a further object of the present invention to provide a method for purifying crude PCNB without causing decomposition of PCNB during distillation under reduced pressure.

It is still another object of the present invention to provide an industrial and easily operable method for producing highly pure PCNB containing 0.3% HCB or less.

According to the present invention, there is provided a method for purifying pentachloronitrobenzene comprising producing a highly purified pentachloronitrobenzene by distilling crude pentachloronitrobenzene containing hexachlorobenzene as an impurity under reduced pressure which comprises treating the crude pentachloronitrobenzene in the molten state or in a mixture solution of nitrobenzene or chloronitrobenzenes with an inorganic basic substance and then distilling the crude pentachloronitrobenzene thus treated under reduced pressure.

DESCRIPTION OF THE PREFERRED EMBODIMENTS

As a simple method for removing acid components in crude PCNB, it is generally thought sufficient to melt PCNB and contact the molten PCNB with water. However, since PCNB has a high melting point (146° C.) and such contact of the molten PCNB with water should be carried out under a considerably high pressure and therefore there are problems from the standpoints of installation and safety.

In the meantime, inorganic bases such as sodium carbonate, potassium carbonate and the like are insoluble in nitrobenzene, chloronitrobenzenes and the like and therefore, it is usually considered that even if such solid bases are added to crude molten PCNB heated to the melting point or higher, the solid bases do not effectively act to neutralize acids in crude PCNB due to their insolubility.

In spite of such considerations, the present inventors tried such method as above. Surprisingly, the present inventors have found that the neutralization reaction smoothly proceeds and acids and inorganic matters are scarcely detected in crude PCNB obtained by removing the precipitated inorganic substances in a hot state through a solid-liquid separating procedure and the resulting pH is neutral. In addition, it has been also found that no decomposition of PCNB is observed when the crude PCNB thus treated is kept below 250° C. upon purification by distillation under reduced pressure and the distillation purification can be effected without problem.

The present invention has been accomplished based on this discovery.

Crude PCNB used in the present invention may be that obtained by chlorination of nitrobenzene or chloronitrobenzenes in chlorosulfonic acid or by the mixed acid nitration of pentachlorobenzene, and the crude PCNB contains tetrachloronitrobenzene, HCB or pentachlorobenzene, HCB, respectively, and further a small amount of acids such as sulfuric acid, hydrogen chloride and the like.

The acid content is not particularly limited, but when an ordinary process is employed, the amount of sulfuric acid in the crude PCNB is about 500–5000 ppm and that of hydrogen chloride is about 100–1000 ppm.

The feature of the method of the present invention is that crude PCNB is treated with an inorganic substance before the crude PCNB is distilled under reduced pressure. The treatment may be conducted by the following simple procedure.

A basic substance is added to molten crude PCNB or to a solution of crude PCNB and nitrobenzene or chloronitrobenzenes such as monochloronitrobenzene, dichloronitrobenzene, trichloronitrobenzene, tetrachloronitrobenzene and the like, and stirred usually for 0.1–5 hours, preferably 0.2–2 hours to neutralize the crude PCNB, and the precipitated inorganic matters are removed by a solid-liquid separating procedure such as filtration. This procedure may be carried out at atmospheric pressure, high pressure, or reduced pressure, and is usually carried out at atmospheric pressure.

When crude PCNB is melted, it is melted at a temperature of the melting point or higher. It is preferable that the temperature is 200° C. or lower so as to suppress the decomposition of PCNB.

When crude PCNB is mixed with nitrobenzene or chloronitrobenzenes to form a solution, the mixing ratio is not particularly limited and the dissolving temperature is not particularly limited as long as it is 200° C. or lower.

As an inorganic basic substance used for neutralizing acids in crude PCNB, there may be used alkaline metal or alkaline earth metal oxides, hydroxides, carbonates or bicarbonates, preferably the carbonates and bicarbonates.

Exemplary suitable inorganic basic substances include lithium carbonate, lithium bicarbonate, sodium carbonate, sodium bicarbonate, potassium carbonate, potassium bicarbonate, calcium carbonate, calcium bicarbonate, magnesium carbonate and magnesium bicarbonate. These basic substances are used in the form of a solid.

The amount of the basic substance is one equivalent or more per equivalent of acid contained in the crude PCNB. The upper limit is not particularly limited, but the amount is usually 10 equivalents or less from an economical point of view. Preferably, it is 1.1 equivalent or more and 5 equivalents or less. Naturally, even when the amount of the basic substance is less than one equivalent per equivalent of acid in the crude PCNB, there is an effect accordingly, but the effect of the present invention is reduced by half. By the pretreatment before distilling crude PCNB under reduced pressure according to the method of the present invention, acids in the crude PCNB can be not only sufficiently removed, but also inorganic salts newly formed by the pretreatment and excess inorganic basic substance used can be almost completely removed by a solid-liquid separation procedure since they are insoluble in crude PCNB.

According to the present invention, crude PCNB produced by a reaction process is pretreated as mentioned above and subjected to a distillation under reduced pressure to give a highly pure PCNB containing only a small amount of HCB.

Distillation under reduced pressure may be carried out as shown below.

Since PCNB thermally decomposes at 250° C. or higher, the pressure in the distillation system is naturally limited by the vapor pressure at that temperature and the vapor pressure at 146° C. (melting point of PCNB), and therefore, the distillation is effected at 3-70 mm Hg, preferably 5-50 mm Hg.

The temperature in the distillation system is kept in the range of from 150° C. (higher than the melting point of PCNB) to 250° C. (lower than the decomposition temperature) as mentioned above.

The column top temperature is 150°-240° C., preferably 160°-220° C., and the bottom temperature is 160°-250° C., preferably 170°-230° C.

The reflux ratio is usually 1-100, preferably 5-50. When the reflux ratio is less than 1, the content of HCB (an impurity) in the PCNB increases while at a reflux ratio higher than 100 the productivity is disadvantageously lowered.

An apparatus for the distillation under reduced pressure may be a continuous or a batch apparatus, and the number of theoretical plates in the distillation column is usually about 1-100 plates, preferably about 5-30 plates.

The type of distillation column and the packing are not particularly critical, but it is preferable to use a type of distillation column and packing which can lower the bottom temperature to a temperature near the melting point of PCNB as far as possible so as to save energy and further can give a very low pressure loss between the column top and bottom as far as possible.

Since impurities such as tetrachloronitrobenzene as a reaction intermediate, HCB and the like contained in crude PCNB have boiling points lower than PCNB, they can be distillated as overhead distillate and the PCNB remaining at the bottom may be obtained as a pure PCNB product, but after removing the impurities as above, if desired, the PCNB product can be further subjected to distillation to produce PCNB of a higher purity.

According to the present invention, it is preferable to carry out the distillation under reduced pressure and in the absence of light.

The present invention is explained further in detail by referring to the following examples.

EXAMPLE 1

In a four-necked flask was placed 400 g. of a crude PCNB [purity: 94%, HCB: 0.6%, tetrachloronitrobenzene: 5.0%, sulfuric acid: 1,450 ppm, hydrogen chloride: 165 ppm] produced by chlorinating nitrobenzene in chlorosulfonic acid and melted by heating to 170° C. To the resulting liquid mixture was added 1.3 g of sodium carbonate powder with stirring and the stirring was continued at 170°-175° C. for one hour. After addition of sodium carbonate, generation of carbon dioxide was observed.

Then the resulting mixture was subjected to filtration in a hot state to remove the precipitated inorganic matters. Analysis of the resulting crude PCNB showed that the contents of sulfate ion and chloride ion were both less than 10 ppm.

350 g of the resulting crude PCNB was placed in a 500 ml egg plant type distillation flask and a distillation column (inner diameter 25 mm φ, height 830 mm, Oldershaw type, number of theoretical plates 12) was fitted to the distillation flask, and a batch distillation was carried out under the following conditions:

| | |
|---|---|
| Bottom temperature | 216-220° C. |
| Column top temperature | 155-180° C. |
| Bottom pressure | 50-65 mm Hg |
| Column top pressure | 10-14 mm Hg |
| Reflux ratio (controlled by a magnet timer reflux controller) | 10 |

Distillation was effected at a distillate speed from the distillation column of 0.08-0.15 g/min and after 4.5 hours 26.4 g of distillate was obtained.

The amount of holdup in the column was 16.9 g, and 305.2 g of purified PCNB was obtained as a bottom residue. The purity of the PCNB was 99.7% and the contents of HCB and tetrachloronitrobenzene were 0.06% and 0.10%, respectively.

EXAMPLE 2

The procedure of Example 1 was repeated except that 2.5 g of potassium bicarbonate was used in place of sodium carbonate. After the treatment with potassium bicarbonate, the inorganic matters were filtered off. The crude PCNB thus obtained contained sulfate ion and chloride ion each in an amount less than 10 ppm similar to Example 1 and the crude PCNB was subjected to distillation under reduced pressure as in Example 1 to obtain 306.3 g of purified PCNB of 99.7% in purity as a bottom residue. HCB and tetrachloronitrobenzene were contained in amounts of 0.08% and 0.12%, respectively.

EXAMPLE 3

450 g of crude PCNB of 98.5% in purity [containing HCB 0.6%, pentachlorobenzene 0.5% and sulfuric acid 2,200 ppm] produced by mixed acid nitration of pentachlorobenzene was melted by heating to 160° C. To the resulting liquid was added 2.0 g of calcium carbonate, the liquid was stirred at 160°-170° C. for one hour, and filtered in the hot state to remove the precipitated inorganic matter.

Analysis of the resulting crude PCNB showed that the content of sulfate ion was less than 10 ppm. 400 g of the crude PCNB was distilled under reduced pressure following the procedure of Example 1 to give 342 g of purified PCNB in 99.8% as bottom residue. The contents of HCB and pentachlorobenzene were 0.08% and trace, respectively. The conditions of the distillation under reduced pressure were as shown below.

| | |
|---|---|
| Distillation column: | 25 mm φ in inner diameter × 830 mm high, Oldershaw type, number of theoretical plates 12 |
| Bottom temperature: | 213-217° C. |
| Column top temperature: | 165-168° C. |
| Bottom pressure: | 46 mm Hg |

-continued

| | |
|---|---|
| Column top pressure: | 7-8 mm Hg |
| Reflux ratio: | 10 |
| Distillate speed: | 0.1-0.2 g/min |
| Time for distillation under reduced pressure: | 4.5 hrs. |
| Amount of distillate: | 38.6 g |
| Amount of holdup in the column: | 19.1 g |

COMPARISON EXAMPLE 1

400 g of crude PCNB used in Example 1 was directly subjected to distillation under reduced pressure without the pretreatment with sodium carbonate. Following the conditions of distillation under reduced pressure of Example 1, the amount of distillate was 31.6 g, the amount of holdup in the column was 17.3 g, and 349.7 g of purified PCNB was obtained as a bottom residue. The content of HCB in PCNB was 0.42% as a result of analysis and thus a significant decrease of HCB as compared with the original content of HCB in PCNB was not recognized. The total amount of HCB in the distillate and the holdup after completion of distillation was 1.8 times the amount of HCB in the crude PCNB. This indicates that HCB was formed during the distillation under reduced pressure.

EXAMPLE 4 AND COMPARISON EXAMPLE 2

Test of Material

Test of material on SUS-304 was effected with respect to crude PCNB before and after the treatment with sodium carbonate in Example 1.

The test was carried out by soaking about a half of the test piece, SUS-304, in molten crude PCNB heated to 200° C. After 200 hours of the test time, the test piece was taken out, washed with acetone and water sufficiently, dried and observed with respect to corrosion.

The results are shown in Table 1, a test piece SUS-304 soaked in the crude PCNB pretreated with sodium carbonate was not substantially corroded and found to be sufficiently corrosion-proof while the other test piece soaked in the crude PCNB not pretreated was clearly corroded.

TABLE 1

| | Test Result | | |
|---|---|---|---|
| | Crude PCNB | Degree of Corrosion (mm/year) | Remarks |
| EXAMPLE 4 | Pretreated with sodium carbonate | 0.02 | Completely corrosion-proof |
| COMPARISON EXAMPLE 2 | Not pretreated with sodium carbonate | 1.38 | Not corrosion-proof |

What is claimed is:

1. A method for purifying pentachloronitrobenzene to produce a highly purified pentachloronitrobenzene comprising treating crude pentachloronitrobenzene containing hexachlorobenzene in the molten state or in a mixture solution of nitrobenzene or chloronitrobenzenes with an inorganic basic substance that is added in solid form and then distilling the crude pentachloronitrobenzene thus treated under reduced pressure.

2. The method according to claim 1 in which the inorganic basic substance is selected from the group consisting of alkaline metal oxides, hydroxides, carbonates and bicarbonates, and alkaline earth metal oxides, hydroxides, carbonates and bicarbonates.

3. The method according to claim 1 in which the inorganic basic substance is selected from the group consisting of alkaline metal carbonates and bicarbonates and alkaline earth metal carbonates and bicarbonates.

4. The method according to claim 3 in which the distillation under reduced pressure is carried out in the absence of light.

5. The method according to claim 1 in which the crude pentachloronitrobenzene has a pH of 4 or less.

6. The method according to claim 5 in which the crude pentachloronitrobenzene contains about 500 to 5,000 ppm of sulfuric acid and 100 to 1,000 ppm of hydrogen chloride.

7. The method according to claim 1 in which the mixture solution contains at least one of monochloronitrobenzene, dichloronitrobenzene, trichloronitrobenzene, or tetrachloronitrobenzene.

8. The method according to claim 1 in which treatment of the crude pentachloronitrobenzene is for 0.1 to 5 hours.

9. The method according to claim 8 in which treatment of the crude pentachloronitrobenzene is for 0.2 to 2 hours.

10. The method according to claim 1 in which the pH of the crude pentachloronitrobenzene is 4 or less and an equivalent ratio of the inorganic basic substance to acidic substance is from 1.1 to 5.0.

11. The method according to claim 1 in which the distilled pentachloronitrobenzene has a content of hexachlorobenzene of 0.3% by weight or less.

12. The method according to claim 1 in which the distillation under reduced pressure is carried out in the absence of light.

13. The method according to claim 2 in which the distillation under reduced pressure is carried out in the absence of light.

14. The method according to claim 1 in which inorganic substances including any remaining inorganic basic substance are removed from the crude pentachloronitrobenzene by solid-liquid separation prior to the distillation of the crude pentachloronitrobenzene.

15. The method according to claim 14 in which the solid-liquid separation is filtration.

* * * * *